US00PP30559P2

(12) United States Plant Patent

Klemm et al.

(10) Patent No.: US PP30,559 P2

(45) Date of Patent: Jun. 4, 2019

(54) *PETUNIA* PLANT NAMED 'KLEPH17300'

(50) Latin Name: *Petunia hybrida*
Varietal Denomination: KLEPH17300

(71) Applicant: Klemm+Sohn GmbH & Co. KG, Stuttgart (DE)

(72) Inventors: Nils Klemm, Stuttgart (DE); Antonella Capo, Latina (IT)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 0 days.

(21) Appl. No.: 15/998,602

(22) Filed: Aug. 16, 2018

(30) Foreign Application Priority Data

Mar. 13, 2018 (QZ) ..... PBR 2018/0754

(51) Int. Cl.
*A01H 5/02* (2018.01)
*A01H 6/82* (2018.01)

(52) U.S. Cl.
USPC ..... Plt./356.2
CPC ..... *A01H 6/82* (2018.05); *A01H 5/02* (2013.01)

(58) Field of Classification Search
USPC ..... Plt./356.2, 356.18
CPC ..... A01H 6/82; A01H 5/02
See application file for complete search history.

*Primary Examiner* — Kent L Bell
(74) *Attorney, Agent, or Firm* — Barbara Campbell; Cochran Freund & Young LLC

(57) ABSTRACT

A new *Petunia* plant particularly distinguished by large, purple flowers and a trailing habit, is disclosed.

1 Drawing Sheet

Genus and species: *Petunia hybrida.*
Variety denomination: 'KLEPH17300'.

CROSS-REFERENCE TO RELATED APPLICATIONS

This application claims priority to and the benefit of European Community Plant Variety Rights application filed on Mar. 13, 2018, File No. 2018/0754, the entire contents of which are incorporated herein by reference for all purposes.

'KLEPH17008' has not been made publicly available for more than one year prior to the effective filing date of the present application.

BACKGROUND OF THE NEW PLANT

The present invention comprises a new and distinct variety of *Petunia*, botanically known as *Petunia hybrida*, and hereinafter referred to by the variety name 'KLEPH17300'. 'KLEPH17300' originated from a cross-pollination conducted in July 2012 in Latina, Italy between the female *Petunia* variety, 'Duesurmar', also commercially known as SURPRISE 'Marine' (U.S. Plant Pat. No. 21,673) and the male *Petunia* variety VIVA 'Blue Ocean' (patent status unknown).

The seeds from the cross were sown and plants were grown in a greenhouse for evaluation, where an individual plant designated 'KLEPH17300' was selected from the group of plants in April 2013 in Latina, Italy. In May 2013, 'KLEPH17300' was first vegetatively propagated by terminal tip cuttings in Latina, Italy. 'KLEPH17300' was found to reproduce true to type in successive generations of asexual propagation via tissue culture and terminal tip cuttings.

SUMMARY

The following are the most outstanding and distinguishing characteristics of this new variety when grown under normal horticultural practices in Stuttgart, Germany and Latina, Italy.

1. Large, purple flowers; and
2. A trailing habit.

DESCRIPTION OF THE PHOTOGRAPH

This new *Petunia* plant is illustrated by the accompanying photograph of a plant grown in a plastic greenhouse in Stuttgart, Germany. The photograph was taken in May 2016 and shows the foliage and flowers of a 12-week-old plant grown in a pot. The colors shown are as true as can be reasonably obtained by conventional photographic procedures.

DESCRIPTION OF THE NEW VARIETY

The following detailed descriptions set forth the distinctive characteristics of 'KLEPH17300'. The data which define these characteristics were collected from asexual reproductions carried out in Latina, Italy. Data was collected on plants grown 16-weeks from cultivation from potting in a plastic greenhouse in Latina, Italy in April 2018. Color references are to The R.H.S. Colour Chart of The Royal Horticultural Society of London (R.H.S.), 5$^{th}$ edition (2007).

Classification:

*Family.*—Solanaceae.
*Botanical.*—*Petunia hybrida.*
*Common.*—*Petunia.*
*Designation.*—'KLEPH17300'.

Parentage:

*Female parent.*—The female *Petunia* variety, 'Duesurmar', also commercially known as SURPRISE 'Marine' (U.S. Plant Pat. No. 21,673).

*Male parent.*—The male *Petunia* variety VIVA 'Blue Ocean' (patent status unknown).

Plant:

*Vigor*.—Medium-high vigor.

*Habit*.—Trailing.

*Height* (*from top of soil*).—10.0 cm to 12.0 cm.

*Width* (*horizontal plant diameter*).—22.0 cm for the plant body; 52.0 cm to 60.0 cm including the flowering stems.

*Propagation*.—Terminal tip cuttings and tissue culture.

*Time to produce a finished flowering plant*.—About 2 weeks.

*Time to initiate and develop roots*.—2 to 3 weeks.

*Root description*.—Moderate density, moderate branching, white roots.

Stems:

*Average number* (*basal*).—11.

*Length of basal branches* (*from the base of the stem to the tip*).—30.0 cm to 38.0 cm.

*Internode length*.—2.5 cm to 5.0 cm.

*Diameter of branches* (*from midpoint*).—0.4 cm.

*Stem color*.—RHS 144D.

*Anthocyanin*.—Absent.

*Texture*.—Pubescent.

Leaves:

*Arrangement*.—Opposite.

*Length*.—7.5 cm.

*Width*.—3.3 cm to 5.3 cm.

*Shape*.—Obovate.

*Apex*.—Broad acute.

*Base*.—Attenuate.

*Margin*.—Entire.

*Immature leaf color*.—Upper surface: RHS 137C. Lower surface: RHS 138B.

*Mature leaf color*.—Upper surface: RHS N137C. Lower surface: RHS 138B.

*Texture* (*both upper and lower surfaces*).—Pubescent.

*Venation pattern*.—Arcuate.

*Venation color*.—Upper surface: RHS 144B. Lower surface: RHS 144B.

*Petioles*.—Length: 0.4 cm. Diameter: 0.4 cm. Color: Between RHS 144C and RHS 144D. Texture: Pubescent.

Flower buds:

*Shape*.—Irregular oblong.

*Length*.—2.5 cm to 5.5 cm.

*Diameter*.—0.5 cm to 0.8 cm.

*Color at tight bud*.—RHS 90A more towards the tip of the bud and RHS 90B towards the base of the bud.

*Texture*.—Pubescent.

Inflorescence:

*Blooming habit* (*flowering season*).—Continuously flowering during spring and summer.

*Inflorescence type*.—Sympodial, with monochasial growth.

*Number of flowers per node*.—1.

*Lastingness of individual blooms on the plant*.—7 to 10 days.

*Fragrance*.—Absent.

*Flowers*.—Arrangement: Composed of 5 petals fused at the base. Diameter (flower face): 7.4 cm. Depth (total length of flower): 7.0 cm. Throat/Funnel: Length: 4.0 cm. Diameter (at opening): 1.4 cm. Texture: Inner surface: Smooth. Outer surface: Pubescent. Color: Inner surface: RHS N92A. Outer surface: RHS 79B from the margin of the petal to RHS 79D towards the base of the petal and RHS 79A veins. Petals: Color of petals, mature flower (fully opened): Upper surface: Between RHS N89A and RHS N88A. Lower surface: RHS N88B. Apex: Obtuse. Base: Fused. Shape: Funnelform. Margin: Entire. Strength of waviness: Weak. Degree of lobation: Weak. Calyx arrangement: Actinomorphic, composed of 5 sepals. Sepals: Color: Upper surface: RHS 137B. Lower surface: RHS 138A. Length: 1.2 cm to 1.5 cm. Width: 0.4 cm. Shape: Oblong. Apex: Broadly acute. Base: Fused. Margin: Entire. Texture (both upper and lower surfaces): Pubescent.

*Pedicels*.—Color: RHS 144A. Length: 4.0 cm to 7.0 cm. Diameter: 0.2 cm. Texture: Pubescent.

Reproductive organs:

*Stamens*.—Quantity: 5. Shape: Needle with elliptic head. Filament: Length: 1.2 cm to 1.5 cm. Diameter: 0.05 cm. Color: RHS 145D. Anther: Shape: Oblong. Color: RHS N187C. Length: 0.1 cm. Diameter: 0.12 cm. Pollen: Color: RHS 91A. Amount: Moderate.

*Pistils*.—Quantity per flower: 1. Length: 3.0 cm. Stigma color: RHS N186A. Style color: RHS 145A.

Fruit and seed set: No fruit and seed set observed.

Disease and pest/insect resistance: No disease and pest/insect resistance observed.

COMPARISON WITH PARENTAL LINES AND KNOWN VARIETY

'KLEPH17300' is a distinct variety of *Petunia* and is distinguished from its parents as described in Table 1.

TABLE 1

Comparison with Parental Lines

| Characteristic | 'KLEPH17300' | Female Parent 'Duesumar' | Male Parent VIVA 'Blue Ocean' |
|---|---|---|---|
| Petal lobe color fully opened | Upper surface: Between RHS N 89A and RHS N 88A Lower surface: RHS N88B | Upper surface: Close to RHS 88A; venation RHS 187A Lower surface: Close to RHS 87A, venation RHS 187A | |
| | Inner surface: RHS N92A | Close to RHS 79A; venation RHS 187A | |
| Flower throat color fully opened | Outer surface: RHS 79B to RHS 79D with RHS 79A (veins) | | |
| Flower size | Big flowers | Smaller flowers | |
| Plant habit | Trailing | | Upright and mounding |

'KLEPH17300' is a distinct variety of *Petunia* and differences between 'KLEPH17300' and the commercial variety 'Sunsurfviomi' (unpatented) are described in Table 2.

TABLE 2

Comparison with Similar Variety

| Characteristic | 'KLEPH17300' | 'Sunsurfviomi' |
|---|---|---|
| Flower size | Bigger flowers than 'Sunsurfviomi' | Smaller flowers than 'KLEPH17300' |

We claim:

1. A new and distinct variety of *Petunia* plant designated 'KLEPH17300' as illustrated and described herein.

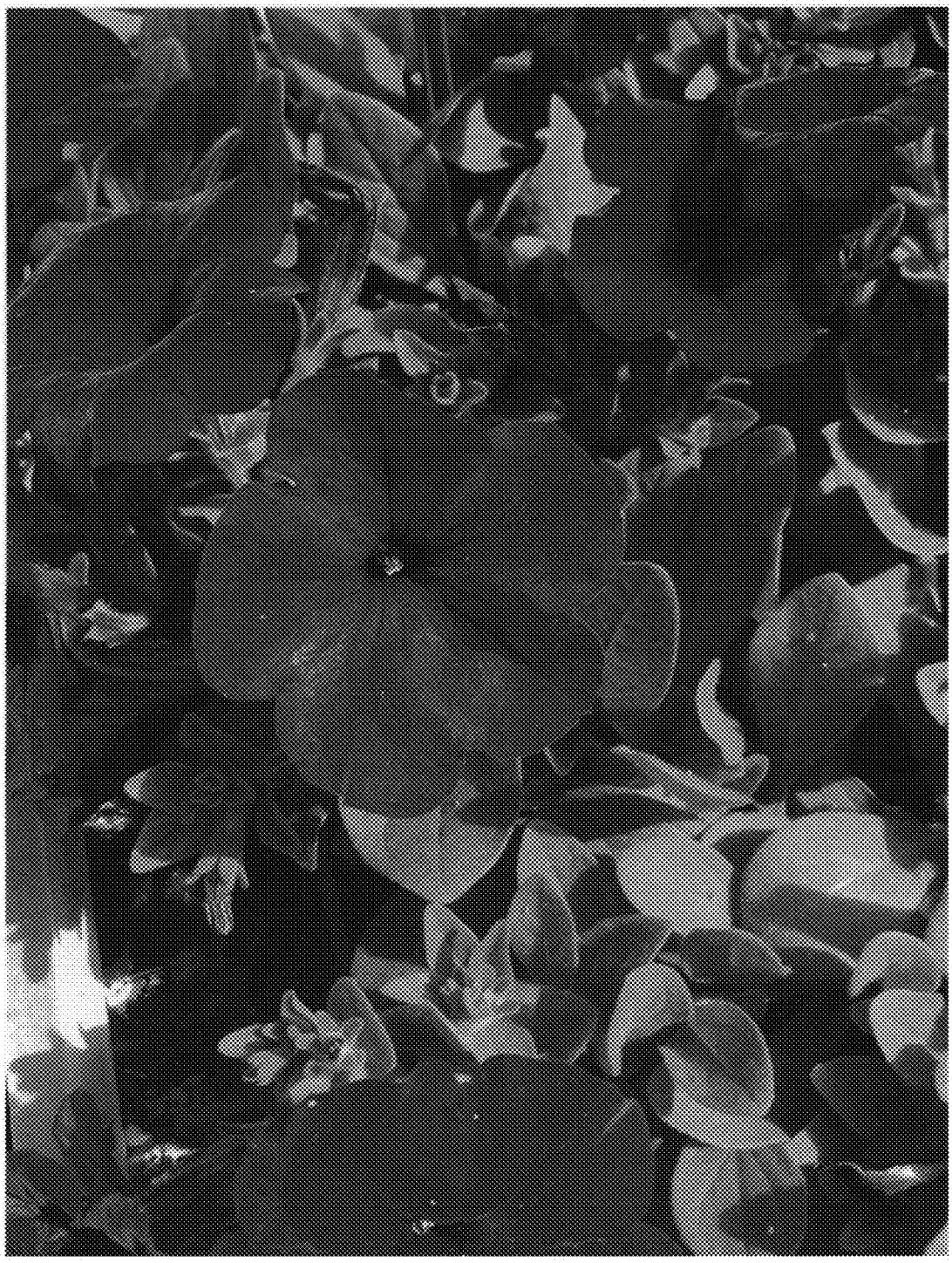

* * * * *